United States Patent [19]

Walch et al.

[11] 4,206,050
[45] Jun. 3, 1980

[54] MEMBRANE UNIT AND APPARATUS FOR REMOVING METABOLITE CONTAMINANTS FROM BLOOD

[75] Inventors: Axel Walch, Frankfurt; Wolfgang Michel, Wiesbaden; Ludwig Lammers, Idstein, all of Fed. Rep. of Germany

[73] Assignee: Hoechst Aktiengesellschaft, Frankfurt am Main, Fed. Rep. of Germany

[21] Appl. No.: 829,942

[22] Filed: Sep. 1, 1977

[30] Foreign Application Priority Data

May 16, 1977 [DE] Fed. Rep. of Germany ....... 2722025

[51] Int. Cl.² .............................................. B01D 13/00
[52] U.S. Cl. .................... 210/23 R; 210/24; 210/321 B; 210/493 M; 210/494 M; 210/500 M; 210/50 Z
[58] Field of Search ................... 210/22, 23, 136, 493, 210/494, 500 M, 502, 321 R, 321 A, 321 B

[56] References Cited

U.S. PATENT DOCUMENTS

| | | | |
|---|---|---|---|
| 3,367,504 | 2/1968 | Westmoreland | 210/321 R |
| 3,670,892 | 1/1972 | Baerg et al. | 210/136 X |
| 3,813,334 | 5/1974 | Bray | 210/321 R |
| 3,827,562 | 8/1974 | Esmond | 210/321 R X |
| 4,048,064 | 9/1977 | Clark | 210/500 M |

*Primary Examiner*—Charles N. Hart
*Assistant Examiner*—Ferris H. Lander
*Attorney, Agent, or Firm*—Schwartz, Jeffery, Schwaab, Mack, Blumenthal & Koch

[57] ABSTRACT

A membrane unit and apparatus for removing toxic metabolites and metabolites normally present in urine from blood is disclosed. The unit comprises an arrangement of at least one permselective membrane and a fluid-absorbing and/or fluid-draining carrier containing at least one adsorbent. The apparatus comprises at least one membrane unit which is connected to inlet and outlet means for transporting blood to and from the unit.

10 Claims, 4 Drawing Figures

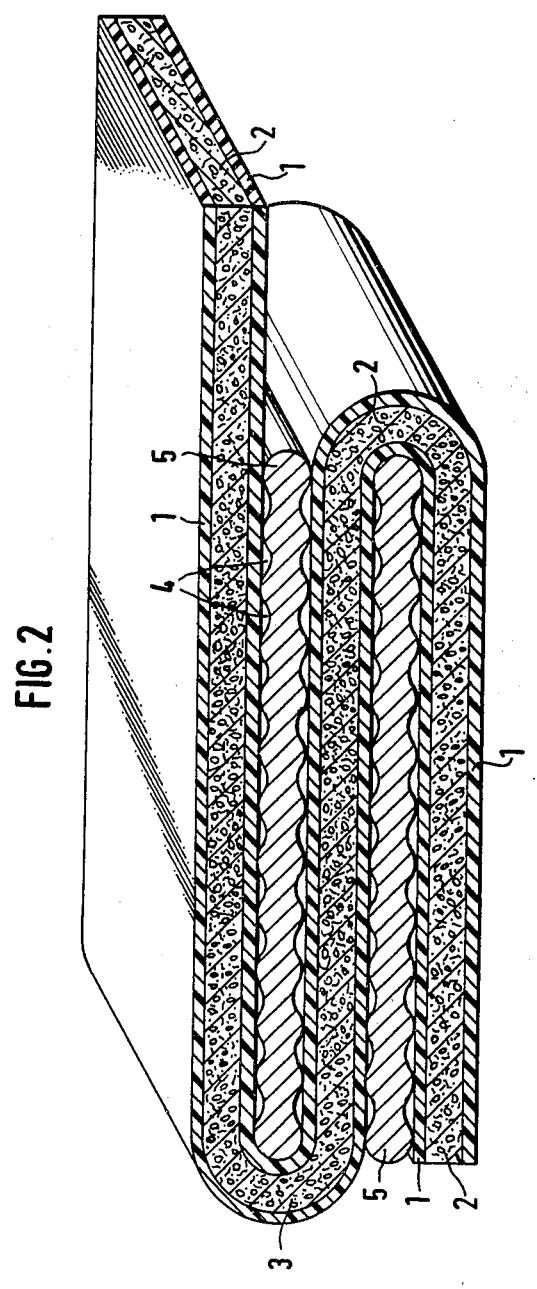

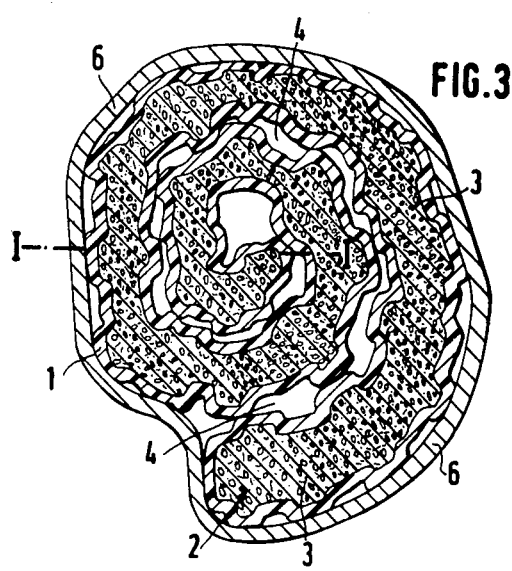
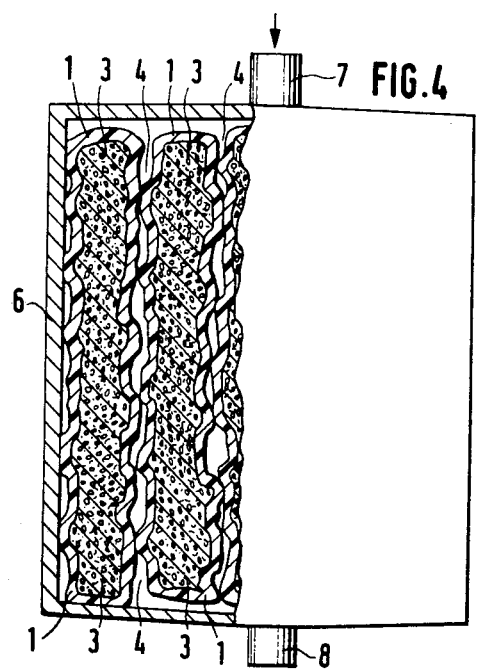

MEMBRANE UNIT AND APPARATUS FOR REMOVING METABOLITE CONTAMINANTS FROM BLOOD

BACKGROUND OF THE INVENTION

1. Field of the Invention:

The present invention relates to a membrane unit, an apparatus comprising a membrane unit and a method for cleaning blood by removing metabolite contaminants, i.e., toxic metabolites and metabolites normally contained in urine, from blood.

2. Description of the Prior Art:

Diafiltration and hemoperfusion are known methods for removing metabolites from blood. Metabolites are those components of the living cells, which control the normal course of metabolic reactions, as well as products of metabolism formed or catabolized in human or animal organisms, such as urea, creatinine, peptides, carbohydrates and electrolytes, e.g., sodium or potassium salts and water. In diafiltration, separation is achieved by means of filtration via selectively permeable membranes hereinafter referred to as permselective membranes. Hemoperfusion is based on the principle of adsorption.

In the diafiltration process the driving force is an adjustable pressure gradient, which determines the transport rate. Any substance having molecules of a size below the porosity limit of the permselective membrane is pressed out as an ultrafiltrate in the same ratio of concentration as in blood. The ultrafiltrate may be rejected; however, a certain portion of the ultrafiltrate extracted from the blood must be returned to the blood stream with all vital substances in a physiological ratio of concentration. Like hemodialysis, diafiltration is primarily used for treating persons suffering from chronic kidney diseases.

Conversely, hemoperfusion is based on a different principle of operation, and its application has been up to now almost exclusively limited to those cases in which a particularly rapid detoxification of the blood is required, as in acute failures of the liver or intoxications. In this method, adsorbents, such as activated carbon or macroporous resins are used to adsorb toxic metabolites. The adsorbents, which are usually enveloped by a porous membrane material, are generally used in granulated form, enclosed as microcapsules in an aqueous suspension, coated upon support webs or used as fiber bundles disposed in columns through which contaminated blood passes. The enveloping of the adsorbents in a porous membrane material is preferred since it prevents direct contact with the blood which improves blood compatibility. Nevertheless, there is a considerable risk of damaging the blood, particularly from loss of blood cells and proteins, from microembolisms due to washed-out adsorbent particles, and from an interruption of the steady flow in the column passed by the blood. In view of this high risk, the use of hemoperfusion is limited to cases in which the patient is comatose.

An additional disadvantage of the hemoperfusion system is that the adsorbent is not adequately capable of adsorbing all metabolites which must be removed from the blood, in particular metabolites normally contained in urine, such as water, urea, electrolytes and ammonia. Even the use of additional complex and expensive measures, such as the use of enzymes, such as urease, in microcapsules, do not result in a simple and satisfactory removal of these metabolites.

It has heretofore been suggested to connect diafiltration and hemoperfusion devices in series in order to utilize the rapid detoxifying action of hemoperfusion and to remove the non-adsorbable metabolites normally contained in urine. This procedure is, however, disadvantageous due to the high blood-filling and residual volume of the devices; in particular, the patient is exposed to the risk of hypotension. Moreover, in addition to the problems inherent in the use of the hemoperfusion device previously described, there is the danger of damaging the blood due to the use of additional, complex apparatus. Finally, it is difficult to coordinate the devices, and further their operation is extremely expensive.

It has also been proposed to lead the ultrafiltrate from a diafiltration device into a device containing toxin-adsorbing substances and subsequently return the detoxified filtrate to the blood stream. In this process heavy metals such as copper are removed by activated carbon and hydrated zirconium oxide. However, such devices operate stepwise and thus have the same disadvantages as a series connection of the devices, particularly due to the high residual volume of the apparatus. Thus, there remains a need in the art for a simple but efficient means of removing metabolite contaminants from blood that avoids the dangers and problems associated with existing systems.

SUMMARY OF THE INVENTION

Accordingly, it is an object of the present invention to provide a membrane unit, for removing toxic metabolites and metabolites normally present in urine from blood, which is only slightly affected by the disadvantages heretofore experienced in the art and which is characterized in particular by simplicity, reduced patient risk and rapid and complete removal of metabolites.

Another object of the invention is to provide an apparatus for the simultaneous removal of toxic metabolites and metabolites normally present in urine from blood.

Still another object of the invention is to provide a method for removing toxic metabolites and metabolites normally present in urine from blood.

The foregoing objects and advantages of the present invention are accomplished by providing a membrane unit which removes toxic metabolites and metabolites normally present in urine from blood, comprising at least one permselective membrane arranged on at least one side of a fluid-absorbing and/or fluid-draining carrier containing at least one adsorbent embedded therein. The arrangement is preferably given a profiled structure.

The membrane unit of the invention may be incorporated into an apparatus for simultaneously removing toxic metabolites and the metabolites normally present in urine from blood by connecting it to one or more inlet and outlet means for transporting the blood to and from the membrane unit.

The membrane unit and apparatus derived therefrom thus provide a simple and efficient method for removing metabolite contaminants from blood by contacting the contaminated blood with the membrane unit and collecting the decontaminated blood from the apparatus.

Other objects and advantages of the present invention will be evident to those of skill in the art after studying

BRIEF DESCRIPTION OF THE DRAWINGS

Some embodiments of the membrane unit arranged in a device are explained in detail by reference to the accompanying drawings of which:

FIG. 2 is a sectional perspective view of another embodiment of the membrane unit;

FIG. 3 is a sectional view of the membrane unit shown in FIG. 1, incorporated in the apparatus according to the invention; and FIG. 4 is a front view, partly in section, of part of the apparatus, along line I—I of FIG. 3.

DETAILED DESCRIPTION OF PREFERRED EMBODIMENTS

Figure 1:
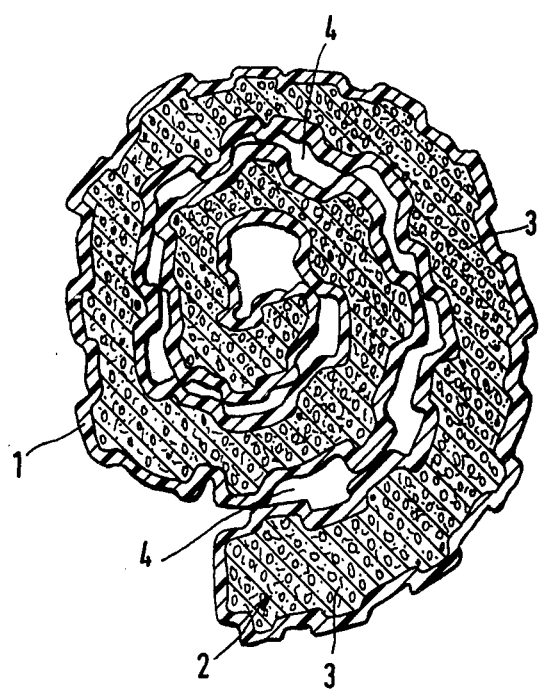
FIG. 1 is a sectional view of a spirally rolled membrane unit.

The blood to be cleaned is led past the side of the permselective membrane which is in contact with the fluid-absorbing carrier, and the ultrafiltrate is absorbed by the carrier. The permselective membrane is composed of materials which are conventionally used in hemodiafiltration and hemoperfusion, such as regenerated cellulose, cellulose ester, cellulose ether, carbohydrate gels, polypeptides, proteins, polyamides, polysulfones, block copolymers with polycarbonate, polymers or copolymers from derivatives of acrylic acid or methacrylic acid, such as nitriles or esters, polymers or copolymers of vinyl alcohol. To facilitate storage, so-called "dry membranes" may be employed, which may be re-dampened prior to use. The size of the pores of the permselective membrane is in the range of about 2 to 10 nm. Optionally, the membrane may be provided with an anti-thrombogenic and biocompatible finish.

The permselective membrane is applied to a fluid-absorbing and/or fluid-draining carrier which is capable of absorbing and/or draining the filtrate and the metabolites contained in the filtrate and into which at least one adsorbent is embedded which binds the toxic metabolites present in the filtrate. The term "embedded" means that the adsorbent is at least at the surface of the carrier, that is, in openings, grooves, channels or depressions. The metabolites which are not adsorbed, particularly water, are taken up by the carrier and if necessary are drawn off. The carrier additionally serves to reinforce and support the membrane so that it is easily handled and damage to the membrane is avoided. The carrier may be made of paper, a woven fabric, a non-woven, a fiber-fleece, a mesh net of synthetic material or a gel-like material. Plates or films having a liquid-conducting profile which may be made of a porous or absorbent material are also suitable carriers. They may be composed of sintered polyethylene, but preferably are made of an absorbent artificial sponge, possibly composed of regenerated cellulose, known as sponge cloth material.

The production of artificial sponge from regenerated cellulose is known to those of skill in the art. Cellulose is first converted into viscose. Reinforcing fiber, such as cotton fiber having a length of 12 to 15 millimeters, may be worked into the viscose, and to enhance pore formation grains of salt, particularly glauber's salt crystals of an appropriate grain size may be included. The composition is then applied to an endless carrier web and precipitated under the influence of heat by a coagulating agent, for example, by a water bath of approximately 100° C. In the water bath a large portion of the salt is dissolved and washed out. Subsequently, the artificial sponge passes a precipitating bath containing aqueous sulphuric acid, a chlorite bleaching bath, if necessary, and an additional washing line, where it is thoroughly washed in water. Finally, the absorbed water is squeezed out and the sponge is dried.

The chemical purity of the artificial sponge must meet strict requirements, comparable to the standards specified for aseptic gauze and gauze bandages made of cellulose. It must not contain toxic compounds or impurities. Thus, the final washing in water during manufacture of the artificial sponge must be thorough, and accordingly, it is preferred to use salt-free water. The addition of dyes or optical brighteners should also be avoided, when the artificial sponge is intended for this particular purpose. In order to reduce clouding of the aqueous extract a cellulose ether is cross-linked on the surface of the artificial sponge and is mixed with a wetting agent to produce hydrophilic properties.

The permselective membrane may be loosely arranged or fixed by bonding, sealing or welding on one or both sides of the fluid-absorbing carrier. Preferably, the membrane layer is prepared directly on the surface of the carrier by coagulation or regeneration of a suitable solution of the membrane-forming substance. The fluid-absorbing carrier may have a profile formed by regularly distributed burls or corrugations, onto which a permselective membrane is applied on one or both sides, so that the membrane itself is profiled.

The adsorbent is present, at least, at the surface of the fluid-absorbing carrier. Its primary function is to bind toxic metabolites. As contemplated by the invention, the adsorbent comprises sheet-like or fibrous bodies as well as granules and powders. The sheet-like or fibrous bodies generally exist as woven, knitted, nonwoven or braided fabrics. By "woven fabric" is meant a sheet-like body composed of warp and weft, while the term "braided fabric" denotes a body similar in structure to a normal wire mesh. The adsorbent is preferably in granulated or powder form.

The materials used as the adsorbents are activated carbon, compounds having ion exchange capacities, such as sulfonated or quaternated polysterene or carbohydrates (e.g., cellulose or sepharose), and hydrophobic synthetic materials such as porous polysterene resin and polyethylene.

The adsorbents are preferably incorporated in the carrier during its manufacture. For example, when an artificial sponge of regenerated cellulose is used as the carrier, the adsorbent is worked into the viscose and thereafter the viscose is coagulated in the usual way. When the adsorbent is composed of a weldable material, such as a polyolefin, polyamide, polyvinyl chloride or polystyrene, the carrier of regenerated cellulose has the additional advantage of being able to be welded to a permselective membrane of a weldable material.

According to another embodiment of the invention, an apparatus for the simultaneous removal of toxic metabolites and metabolites normally contained in urine from blood is provided. This apparatus comprises at least one inlet for the contaminated blood and at least one outlet for the decontaminated blood. Both the inlet and outlet means are connected to the permselective membrane having at least one membrane unit constructed in accordance with the present invention. The apparatus may have one or several outlets for the filtrate, which are connected to the fluid-absorbing carrier.

If the filtrate is not drained off, it is necessary to choose adequate dimensions for the apparatus and to adapt it to the flow and pressure ratios which vary with the absorption of the filtrate. In such cases, the removal of non-adsorbable substances is substantially reduced, and primarily water and adsorbable toxic metabolites are extracted, since the adsorbent changes the balance of the toxic metabolites at the boundary surface of the permselective membrane and the carrier absorbs water.

Various embodiments of the present invention are illustrated by the drawings. FIG. 1 is a sectional view of a spirally rolled membrane unit. It comprises a fluid-absorbing carrier 2 covered on both sides by a permselective membrane 1. Due to its profiled surface the membrane 1 is separated from the opposite permselective membrane. A powdery, granulated, fibrous or sheet-like adsorbent 3 is embedded into the carrier 2, and serves to bind quickly the toxic metabolites.

Blood is introduced vertically to the plane of drawing via an inlet which is not shown. It enters the cavities 4 formed by the profile of the permselective membranes 1, passes the cavities 4 and is subsequently drawn off from the device via an outlet which is not shown. The filtrate penetrating the permselective membrane 1 is absorbed by the carrier 2.

When the permselective membrane 1 has no profile a spacer, for example, in the form of a mesh net, must be provided in order to maintain a cavity through which the blood may pass.

The blood passes the rolled membrane unit in axial direction, although it may also flow in the direction in which the spiral is rolled. In such cases the blood is drawn off centrally or at the circumference of the rolled spiral, depending upon its direction of flow.

The embodiment of the membrane unit shown in a cross-sectional view in FIG. 2 comprises a fluid-absorbing carrier 2 which is folded to form an accordion arrangement and is coated on both sides with permselective membranes 1. At least one adsorbent 3 is embedded into the fluid-absorbing carrier 2 for binding toxic metabolites. Between the adjacent layers of this folded arrangement spacers 5 with corrugated surfaces are disposed which maintain a cavity through which the blood may pass. When the fluid-absorbing carrier and thus the membrane are profiled, the spacers may be omitted.

The apparatus shown in FIGS. 3 and 4 comprises a shell 6 provided with an inlet 7 for the contaminated blood and an outlet 8 for the decontaminated blood. Reference numerals 1 to 4 correspond to the reference numerals given in FIG. 2. Draining off of the filtrate from the fluid-absorbing carrier layer 2 is not included.

For reasons of clarity the membrane units shown in FIGS. 1 to 4, the inlet 7 and the outlet 8 are not shown true to scale, as far as thicknesses and lengths are concerned. In practice, the membrane unit will usually have thicknesses ranging from about 0.5 to 3 millimeters. Thus, a plurality (50 to 100) of the windings shown may be incorporated in the apparatus.

By interchanging the layers it is also possible to design the membrane unit in such a manner that the spacer is folded to form an accordion arrangement while the fluid-absorbing carrier with the embedded adsorbent and the permselective membrane is placed between the neighboring layers of the folded arrangement.

Apart from the embodiments of the membrane unit shown in the figures, it is also possible to use membrane units comprising a pile of rectangular or circular plates arranged one behind the other but at a distance from one another. In such cases, a number of feed-in webs corresponding to the number of membrane units are provided for introducing the blood into the individual membrane units, and if necessary, a corresponding number of draining channels are disposed at the opposite ends of the individual membrane units. However, the blood may also be fed into the first membrane unit in the pile and drawn off from the last membrane unit in the pile. If so, the blood may be deflected at the end of each membrane unit and introduced into the neighboring unit, passing in the opposite direction.

The membrane unit and apparatus produced therefrom are excellently suited for the simultaneous removal of toxic metabolites and of metabolites normally contained in urine from blood. The apparatus have a reduced volume and combine the advantages of diafiltration devices with the advantages of hemoperfusion devices, that is, they are easily adapted for separating water, electrolytes, urea and ammonia and also toxic metabolites from blood.

The membrane unit and purification apparatus thus provide an improved method for removing toxic metabolites and metabolites normally present in urine from blood. This method is characterized in that a sheet-like permselective membrane is used to remove metabolites normally contained in urine as well as toxic metabolites and in that the filtrate which has penetrated the membrane is simultaneously led over at least one adsorbent for adsorbing toxic metabolites.

If the filtrate is drawn off by way of one or several outlets connected with the carrier, part of the substances extracted from the blood which are essential for the organism must be replaced in a physiological concentration by means of a replacement liquid in a manner similar to that of diafiltration. When a replacement liquid is not supplied and the filtrate is not drawn off, the filtrate is absorbed by the absorbent carrier, and primarily water and adsorbable toxic metabolites are removed.

While the invention has been described in terms of various preferred embodiments, the skilled artisan will appreciate that various modifications, substitutions, omissions, and changes may be made without departing from the spirit thereof.

What is claimed is:

1. A membrane unit for simultaneously removing toxic metabolites and metabolites normally present in urine from blood, comprising at least one permselective membrane having a pore size capable of selectively removing from blood toxic metabolites and metabolites normally present in urine, to produce a filtrate containing said metabolites, said permselective membrane being arranged on at least one side of a carrier comprising an artificial sponge composed of regenerated cellulose, said carrier being adapted to absorb and hold the filtrate and metabolites contained in the filtrate, and embedded in said carrier at least one adsorbent capable of adsorbing the toxic metabolites contained in the filtrate.

2. A membrane unit as defined by claim 1, wherein said fluid-absorbing carrier and said permselective membrane are given a profiled structure.

3. A membrane unit as defined by claim 1, wherein said adsorbent comprises a compound selected from the group consisting of activated carbon, a compound having an ion exchange capacity, a hydrophobic synthetic material and a porous synthetic resin.

4. A membrane unit as defined by claim 1, wherein said unit is rolled into a spiral configuration.

5. A membrane unit as defined in claim 1, wherein said unit is folded to form an accordion configuration.

6. An apparatus for simultaneously removing toxic metabolites and metabolites normally contained in urine from blood comprising a membrane unit as defined by claim 1 connected to at least one inlet means for admitting contaminated blood and at least one outlet means for releasing decontaminated blood.

7. An apparatus as defined in claim 6, wherein a plurality of membrane units arranged side by side are connected to said inlet and outlet means.

8. A method for simultaneously removing toxic metabolites and metabolites normally present in urine from blood, comprising the step of contacting the contaminated blood with a membrane unit as defined by claim 1, whereby toxic metabolites and metabolites normally present in urine are separated from the blood in the form of a filtrate, said toxic metabolites are adsorbed by said adsorbent, and the remainder of the filtrate is absorbed by said carrier.

9. A membrane unit as defined by claim 1, wherein said at least one permselective membrane forms at least one cavity through which the contaminated blood passes.

10. A membrane unit as defined by claim 9, wherein said cavity is formed by a spacer disposed between two surfaces of the permselective membrane.

* * * * *